(12) United States Patent
Maget et al.

(10) Patent No.: US 6,383,165 B1
(45) Date of Patent: May 7, 2002

(54) SYSTEM FOR ACHIEVING A CONTROLLED LOW EMISSION RATE FOR SMALL VOLUMES OF LIQUID SOLUTIONS

(76) Inventors: Henri J. R. Maget, 2661 Palimino Cir., La Jolla, CA (US) 92037; Robert J. Rosati, 7749 Palacio St., Carlsbad, CA (US) 92009

( * ) Notice: Subject to any disclaimer, the term of this patent is extended or adjusted under 35 U.S.C. 154(b) by 0 days.

(21) Appl. No.: 09/668,501

(22) Filed: Sep. 22, 2000

(51) Int. Cl.⁷ .............................................. A61M 37/00
(52) U.S. Cl. ........................ 604/141; 604/132; 604/145; 604/131; 422/1
(58) Field of Search .............................. 422/1; 604/141, 604/132, 145, 131

(56) References Cited

U.S. PATENT DOCUMENTS

| | | | | |
|---|---|---|---|---|
| 4,902,278 A | * | 2/1990 | Maget et al. ................ | 604/132 |
| 5,928,194 A | * | 7/1999 | Maget ........................ | 604/141 |
| 5,938,640 A | * | 8/1999 | Maget et al. ................ | 604/145 |

* cited by examiner

Primary Examiner—Robert J. Warden, Sr.
Assistant Examiner—Sean E. Conley
(74) Attorney, Agent, or Firm—Garles C. Logan II

(57) ABSTRACT

A system for achieving a controlled low emission rate of small volumes of liquid solutions for pest and insect management and other applications. The system has a sealed liquid solution reservoir having an outlet port, a self-powered fluid delivery micropump, and a collector for receiving a liquid solution from the sealed liquid solution reservoir. The liquid solution reservoir has a small volume capacity in the range of 1–100 mL. The micropump is a fluid transfer device capable of delivering 1–1000 microliters/hour of liquid solution. The collector has a low emission rate in the range of 0.1–2000 mg/day. The micropump and the sealed liquid solution reservoir may be contained in a single assembly. Also the entire structure of the system may be located in a single container that may be attached to a support structure. The system also allows a multicomponent mixture in the reservoir to be delivered to a collector such as a blotter that allows the different chemical agents to emanate therefrom at a constant ratio throughout the term of the operation.

30 Claims, 4 Drawing Sheets

SYSTEM FOR ACHIEVING A CONTROLLED LOW EMISSION RATE FOR SMALL VOLUMES OF LIQUID SOLUTIONS

BACKGROUND OF THE INVENTION

The invention relates to fluid delivery applications and more specifically to a system for achieving a controlled low emission rate for small volumes of chemical agents for pest and insect management. The emission of chemical agents such as insecticides, pesticides, pheromones, etc. to control pests, frequently requires controlled and accurate rates of delivery, if specific results, such as kill rate, mating interruption, aggregation prevention, etc., have to be achieved, effectively. Whenever multi-component chemical agent blends are required, it is extremely difficult to achieve and maintain the desired emission rates, using existing delivery devices, or emitters.

The examples recited below from published experiments, illustrate the need for release control and show that available devices do not satisfy this need.

In Japan, the tea tortrix is a serious pest, on tea plants. Pest control can be achieved by mating disruption, using Z-11-TDA (Z-11 tetradecenylacetate) as the mating interruption pheromone. In these experiments, it was possible to show the following agent activity.

| Release rate of Z-11-TDA (mg/day/hectare) | Mating ratio % |
|---|---|
| 1300 | 68 |
| 2000 | 45 |
| 3500 | 20 |

Mating disruption is proportional to pheromone release rate. Therefore, the emitter, preset for a specific rate, should sustain it, since mating is not appreciably prevented below rates of 2000 mg/day/ha. Furthermore, since different dose rates are needed in different areas, the emitter should be flexible enough to accommodate different rates.

In another controlled test, small moths (Prays oleae), lured by PBX, were trapped in five successive time periods by four different doses, ranging from 0.1 to 20.0 mg. The dose-response relationship, reported below, points to a maximum catch, at 1.0 mg, which is twice that for any other doses.

| | | Mean catches with lure doses of | |
|---|---|---|---|
| | 0.1 mg | 1.0 mg | 5.0 mg |
| Time sequence | | | |
| Year 1981 Oct 04 | 18.0 | 56.8 | 24.3 |
| Oct 09 | 31.3 | 70.8 | 24.3 |
| Oct 14 | 39.3 | 68.0 | 31.3 |
| Oct 18 | 43.7 | 43.2 | 40.0 |
| Oct 21 | 6.7 | 17.8 | 13.3 |
| TOTAL | 139.0 | 260.6 | 152.9 |

Obviously, the effectiveness of the trap is strongly affected by the ability to maintain a 1.0 mg dose.

In Western Europe, four species of tortridid moths infest fruit orchards. All species use dodec-8-en-1-ol acetate (8-12-26 Ac) as major component, available as (Z) or (E) isomers. However, 100% attractivity towards the binary mixture is achieved in the following manner:

| |
|---|
| 5% of (E) isomer in the blend attracts G(Grapholita) funebrana |
| 10% of (E) isomer in the blend attracts G-molesta |
| 25% of (E) isomer in the blend attracts G-janinthana |
| 90% of (E) isomer in the blend attracts G-iobarzewski |

In this case, the integrity of the species is maintained by differentiating blend compositions. Therefore, if both isomers are not emitted at the appropriate rate, multiple species may be attracted.

In British Columbia (1991), verbenone was tested as an anti-aggregation pheromone for mountain pine beetle. At an emission rate of 3.8 mg/day, from a concentrated source, the pheromone completely inhibited response to an attractant blend consisting of myrcene, exo-brevicomin and trans-verbenol. When verbenone was released from beads on the forest floor, effectiveness was reduced by 50%. When exposed to sunlight, 50% of verbenone was converted to the inactive chrysanthenone, within 75 to 100 minutes. Rapid isomerization probably reduced verbenone concentration to below biologically active levels. This illustration points to the specific need of point sources and to the danger of exposing the pheromone to sunlight.

Similarly, in another antiaggregation experiment, an optimum dosage of verbenone was determined to reduce infestation of mountain pine beetle in lodgepole pines in Central Idaho.

The results of the previous experiments are used as a way to illustrate the critical nature of pheromone concentration, the narrow concentration ranges for effectiveness, the need to emit from concentrated, or point, sources, and the specificity of the emission rate. Point sources are only symptomatic of the need to create a repeatable concentration gradient to which the insects are responding.

Pheromone dispensers can be grouped in two general classes: passive devices, which are based on natural forces (evaporation, diffusion, etc.) and active devices which require man-made energy sources (batteries, springs, etc.)

Passive Devices

Plastic Laminate Dispensers contain pheromone trapped between layers of plastic films. The emission rate is proportional to the inverse of square root of time, such that Rate=a $t^{-\frac{1}{2}}$ where (a) is a characteristic of film properties and geometry. Devices of this type display a high initial emission rate progressively decreasing to zero. This behavior is characteristic of first order kinetics, i.e. the rate is concentration-dependent. Since the coefficient (a) is also dependent on the properties of the pheromone, it is 1) difficult to control the rate, and 2) in the case of multicomponent blends it is not possible to control the concentration ratios of individual components. Hollow fibers are used as capillaries from which the pheromone diffuses through the vapor-air volume, considered the rate-controlling step. Therefore, the rate should be predictable. However, liquid retention within walls and fiber cross-channels result in a release rate between order zero and one commercial success is further hampered by the financial investment in the equipment required to process the fiber bundles.

Microcapsules consist of packaging chemicals in a microgranular form with stabilizing agents. The 1–1000 microns diameter capsule contains the pheromone which is therefore protected from the environment, i.e. light and oxygen. Again, since the active ingredient concentration within the capsule changes with time, the emission rate is first order, i.e. time-dependent.

Other dispensers have also been developed and used. They include polyethylene tubes, rubber septa, polyvinyl chloride rods or pellets, cigarette filters, polyethylene vial caps, dental roll, etc.

In summary, none of the existing and currently-in-use dispensers can achieve the "ideal" zero-order delivery, or the sustained release of multiple pheromones at concentration ratios required for an effective use of generally expensive chemical agents.

It will be the primary object of the present invention to show that "ideal" control release is achievable.

Active Devices

Timed release spray dispensers have been used for mating interruption of the blackheaded fireworm. A battery-powered timing mechanism operating a valve is used to spray the sex pheromone solution at preset time intervals. Spray dispensers are nearly zero-order release devices. However, the intermittent delivery results in "spurt" emission, thereby creating a discontinuous release.

The object of this invention will be to demonstrate "continuous" emission.

Although the previous examples specifically describe pheromones, the present invention is also suitable for liquids such as fragrances, insect formulations, sanitizers, disinfectants, repellents, aromatherapuetic formulations, or any other such liquid requiring delivery in a controlled manner.

The following summarizes certain desired dispenser features and attributes and emitter characteristics, albeit not necessarily achievable simultaneously.

Compatibility with most pheromones

Compatibility with a variety of solvents, diluents, additives, ranging from water to functional chemicals to hydrocarbons Compatible with multicomponent blends Maintaining the relative concentration ratios of all components in solution Long term (6 months) storage of the pheromone in the dispenser without adverse effects (evaporation, phase separation, chemical changes, etc.)

Protection from light, UV and oxygen

Release at "quasi" steady state (zero-order)

Release of multicomponent blends without affecting individual component rates

Readily changeable delivery rate, i.e. use of the dispenser for a variety of different rates, with minor changes.

Long term delivery capability

Ease of filling and sealing the reservoir

Ease of start-up

Small investment in filing/sealing equipment

Ease of field placement

Economical

SUMMARY OF THE INVENTION

The object of the present invention is to satisfy most, or all, of the desirable features of dispensers described above, with emphasis on constant release rate for long time periods and the maintenance of the desired concentration ratios throughout release.

Constant release rates of fluids can be achieved by using pumps. However, since pheromone delivery rates are of the order of 5 to 50,000 micrograms/hour (5 nanoliter to 50 microliters/hour) no practical economical delivery devices are available at the nanoliter/hour rate although they are available at the microliter/hour rate. Therefore, by selecting appropriate solvents, it is possible to increase the release rate to the practical microliter/hour level.

Since emanation of pheromone has to be performed over long time periods, i.e. 100 days or more (2400 hours) the total fluid volume should be maintained within manageable limits, i.e. 5 to 25 mL.

A suitable fluid delivery pump with pre-set or programmable flow rates to achieve a time-dependent fluid delivery profile, which includes a power source that can be a battery or wall power, a pumping mechanism and fluid reservoir, has already been described in previous patents, namely Maget et al in U.S. Pat. No. 4,902,278; Maget in U.S. Pat. No. 5,928,194 where examples of devices operating at rates of 3.3 to 4.4 microliters/hour are reported, expelling liquid from the reservoir to a matrix material, and in U.S. Pat. No. 5,938,640 (Maget et al) which describes a fluid dispenser with a re-usable pumping module and disposable reservoir.

Electrochemical pumps, of the type described in U.S. Pat. No. 4,902,278 have been operated "outdoors" for periods to 35 days, maintaining a constant flow rate of 11.1 microliters/hour, while dispensing a multicomponent fluid consisting of a diluent (ethylene glycol) and a ternary pheromone mixture consisting of verbenone, ipsdienol and methylcyclohex-enone.

Electrochemical pumps can operate with a variety of fluids, including many solvents such as ethanol, water, heptane, ethylene glycol, butanediol.

The next step following controlled release of the fluid is the capture, dispersion and retention of the solvent/pheromone mixture by a collector from which solvent and pheromone can evaporate and emanate.

Suitable fluid collectors are absorbent pads located adjacent to the fluid release channel, which receive the mixture, disperse it by wetting the pad, and from which solvent and pheromone can evaporate, albeit at different rates.

For example, if the solvent is heptane, the evaporation rate is substantial and dispersion is minimal. If the diluent is ethylene glycol, the evaporation rate is low and considerable invasion of the pad will take place.

Emanation of the pheromone is the subsequent step. Although pheromone vapor pressures can be rather low (less than 0.5 mm Hg for a solid such as verbenol) the evaporation surface can be substantial and therefore the pheromone emanates nearly instantaneously without accumulation on the pad.

In most instances, the emanation rate of the pheromones exceeds the fluid delivery rate (and therefore the emanation rate is identical to the fluid delivery rate), thus achieving a zero-order emission.

GLOSSARY

Additive—a substance added to another in relatively small amounts to impart or improve desirable properties or suppress undesirable properties (such as a stabilizer to prevent the action of light or an antioxidant to prevent degradation by oxygen).

Aromatherapy—a treatment involving fragrants or strong scents.

Chemical agent (s)—a natural or synthetic compound or blend formulated for a specific action.

Diluent—an agent that makes thinner or less concentrated by admixture.

Dispenser—a device releasing material (gas, liquid or solid).

Electrochemical pump—a pumping device based on the use of an electrochemical process: electrolysis, oxygen enrichment from air, galvanic reaction, resulting in gas generation.

Electromechanical pump—an electrically or electronically controlled pump.

Emanate—to come from a source.

Emission—the act of discharging (into the air).

Emitter—a device that sends out.

First-order—a reaction or process which decreases progressively with time.

Fragrance—a sweet or delicate odor.

Gas pump—a pumping device based on the use of gases generated through chemical reaction, or stored gas (carbon dioxide generator-based pump, Freon pump, carbon dioxide stored pump).

Mechanical pump—a pumping device using mechanical stored energy such as a spring.

Pesticide, Insecticides—an agent that destroys pests or insects.

Pump—device used to transfer a liquid from one location to another.

Pheromone—a chemical released by an animal for a specific purpose.

Semiochemical—chemical involved in communication by insects.

Solvent—chemical capable of dissolving or dispersing one or more chemicals.

Zero-order—a reaction or process which is constant with time.

DESCRIPTION OF THE PREFERRED EMBODIMENT

Figure 1:
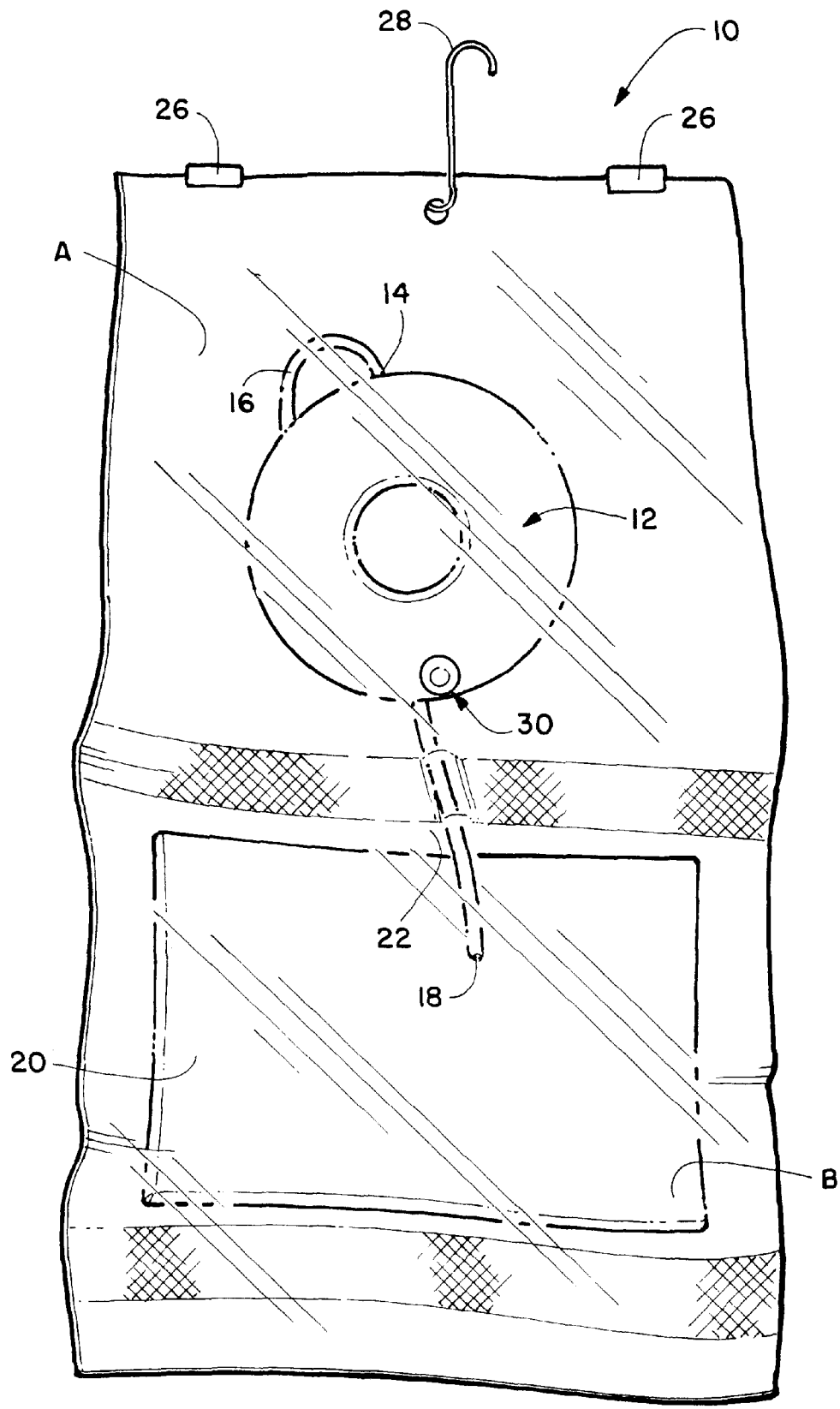
FIG. 1 is a front elevation view of an embodiment of the system showing all of the components in a single container.

A preferred embodiment of the system is illustrated in FIG. 1. The preferred emitter consists of an autonomous, totally integrated pumping system. It has a container 10 formed from a porous material rear wall and a plastic film front wall. It has chambers or compartments A and B. A self-powered fluid delivery micropump 12 is positioned in chamber A and it has an outlet port 14 connected to a length of tubing 16 having a distal end 18. An absorbant pad or blotter 20 is located in chamber B. The distal end 18 of tubing 16 passes through an aperture 22 between chambers A and B. Chamber B is essentially a sealed compartment and the chemical agents can emanate through the porous material which also protects the collector from the environment. One or more clamps 26 normally close the top end of the chamber A prior to its installation for use. A hook 28 may be used for easy attachment or placement on trees, animals, or such-like carriers.

The micropump 12 has a fill port, such as a septum or inlet port valve 30 that allows a liquid solution to be injected into the reservoir in the micropump assembly.

Figure 2:
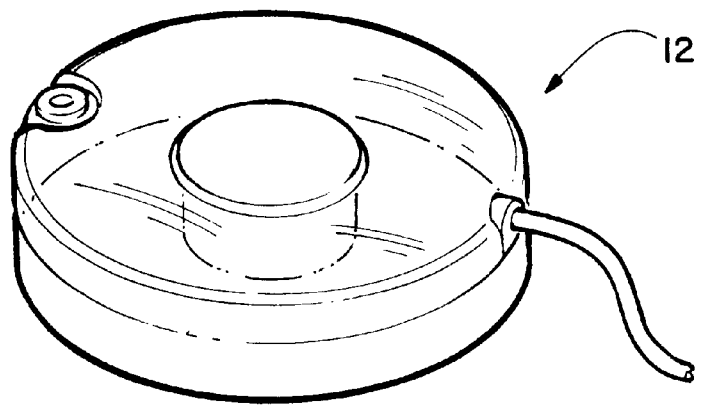
FIG. 2 is a front perspective view illustrating one of a number of micropumps that could be used with the system.
Figure 3:
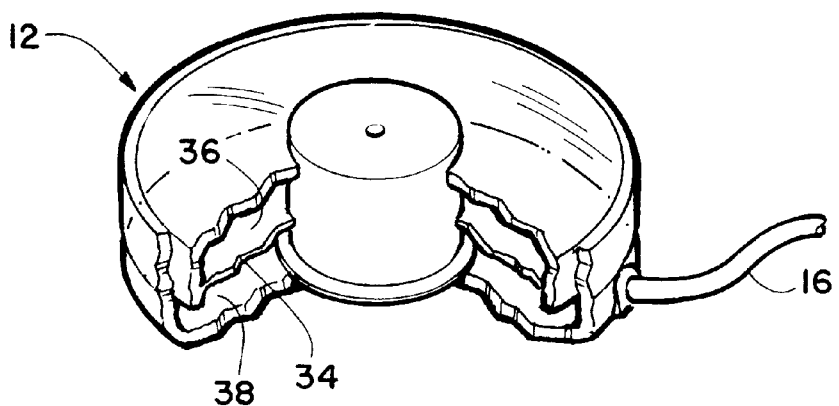
FIG. 3 is a front perspective view of the pump illustrated in FIG. 2 with portions broken away.

FIGS. 2 and 3 illustrate an electrochemical micropump 12 that can be used in the system. The structure of the micropump is of the type that is described in U.S. Pat. No. 4,902,278. It has an electrochemical cell 32 and a gas cavity 34. A diaphragm 36 separates gas cavity 34 from the reservoir 38 that contains a liquid solution. Reservoir 38 has a capacity of 5–25 mL. The micropump has a fluid flow rate of 5–25 microliters/hour, thus operable for durations of 1 to 30 weeks, powered by commercially available button cells with an energy capacity from 20 to 100 mAhr. The micropump illustrated is 2 inches in diameter and has a height of 0.63 inches. The micropump has an empty weight of 18.6 grams and a fluid volume of 10.0 mL. The 0.3 cm thick blotter 20 has a fluid retention capability of 0.3 to 0.8 mL of solution/cc of blotter, thus an area which does not have to exceed 25 cm , for the worst case use, i.e. when the solvent is completely retained, without evaporative losses.

The pre-filled emitter is started at the time of use by initiating pump operation and opening the fluid delivery channel. No further attention is required during the use period of the emitter.

Figure 4:
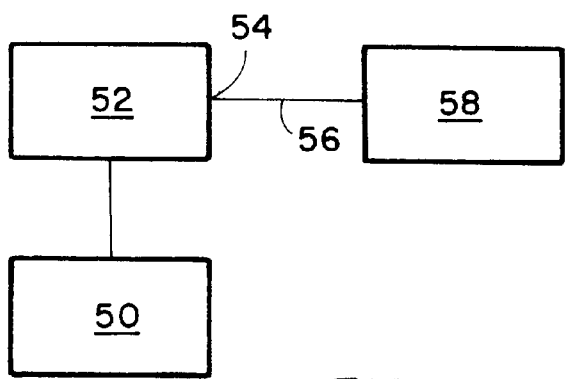
FIG. 4 is a block diagram illustrating the system for achieving a controlled emission rate of small volumes of liquid solution for pest and insect management.

FIG. 4 is a block diagram of the general system for achieving controlled low emission rates of small volume solutions for pest and insect management. A pump 50 is connected to a sealed chemical agents reservoir 52 having an outlet port 54. Outlet port 54 is connected to length of tubing 56 that deposits the liquid solution onto a collector 58. Micropump 50 may be a gas pump, an electromechanical pump, an electrochemical pump or a mechanical pump. Collector 58 may be an absorbant pad such as a blotter with adequate wicking capability to disperse the solution rapidly over as large a surface as available. Collector 58 can also be a tray, a plastic bag, etc., open to the environment. The collector can also be an absorbent pad enclosed by a film extremely porous to allow chemical agents evaporation, while protecting the pad from the environment(rain, wind, debris, etc.).

Figure 5:
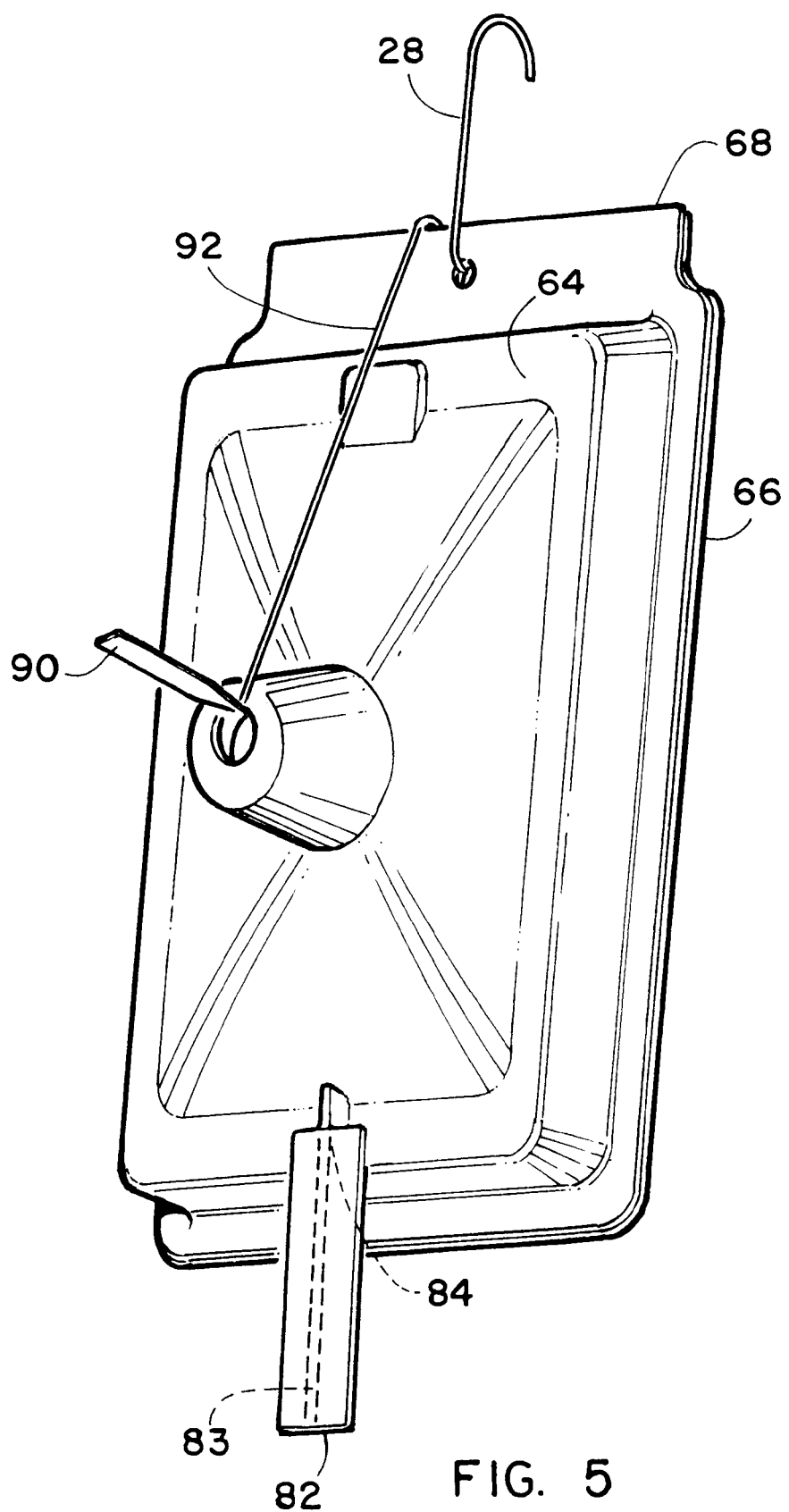
FIG. 5 is a front perspective view of an alternative embodiment of the system showing all of the components in a single container.
Figure 6:
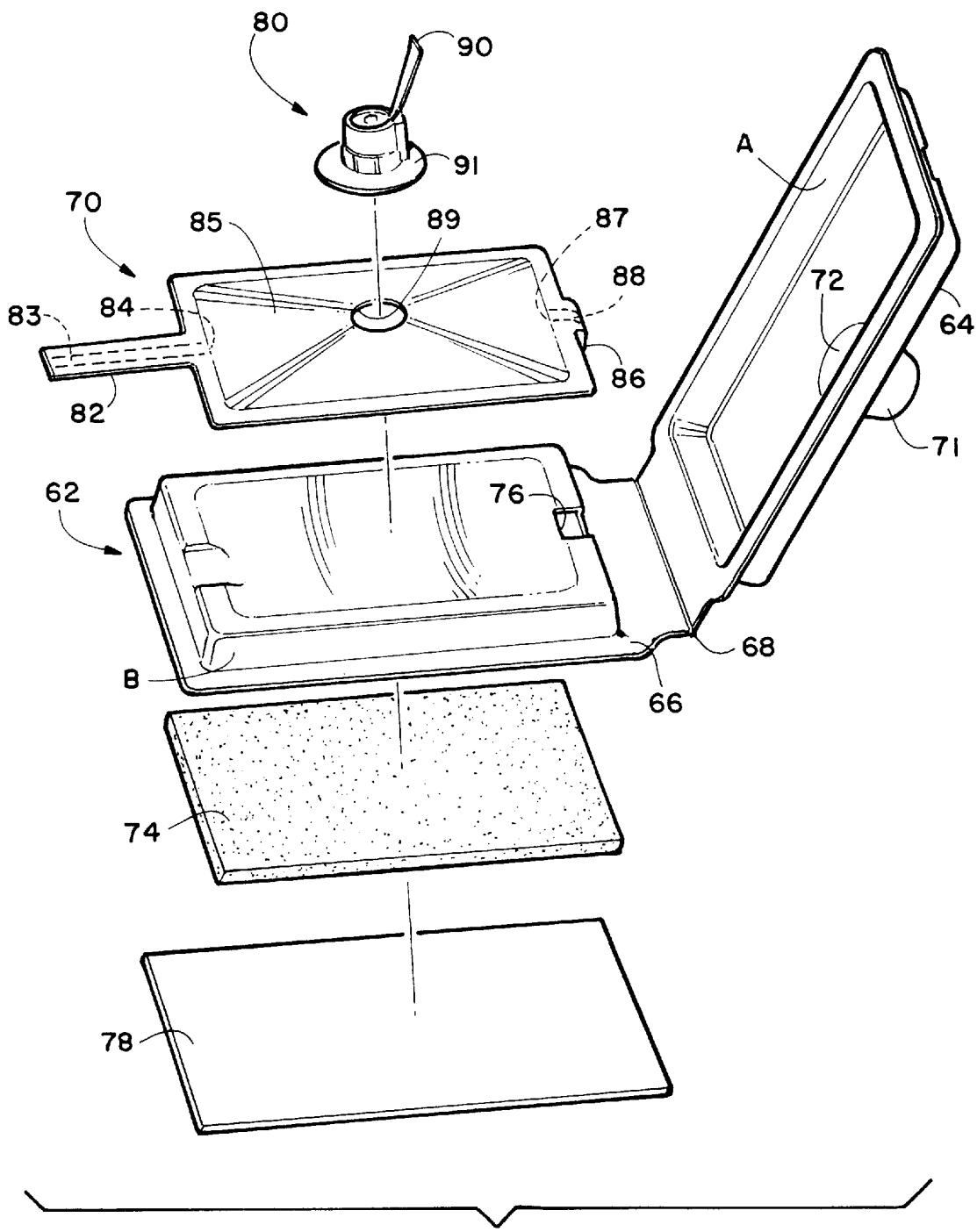
FIG. 6 is an exploded front perspective view of the alternative embodiment of the system.

An alternative embodiment of the system showing all of the components in a single container is illustrated in FIGS. 5 and 6. The container is generally designated numeral 60. It has a plastic clam shell tray 62 having a cover or top panel 64 and a bottom panel 66. The front ends of the respective panels are connected together by a living hinge 68. The bottom surface of top panel 64 has a chamber A formed therein for receiving the sealed liquid solution reservoir or pouch 70. A collar 71 extends upwardly from the top surface of top panel 64 and it has a aperture 72 in its bottom end that communicates with chamber A. Bottom panel 66 has a chamber B formed in its bottom surface that receives collector or blotter 74. An aperture 76 in bottom panel 66 provides for communication between chambers A and B. A bottom wall 78 made of a breathable film seals the bottom of chamber B after blotter 74 has been inserted therein.

Reservoir 70 is a foil laminate pouch, with material layers chosen for easy, robust, manufacture and chemical compatibility, that blocks volatile compounds from being lost or reaching the self-powered electrochemical micropump 80, via diffusion during storage and operation. It also protects the liquid solution compounds from the UV light in the field to maximize the ability of the UV sensitive pheromones, and protects the pheromones from the oxygen generated by the pump. A minimum thickness foil was prioritized to maximize flexibility of the film and minimize cost. An adhering material can be applied to pouch outer surface or tray cavity A to attach outer pouch layers to the tray and transfer chamber A shape to the reservoir. This prevents self-emptying of high capillary force liquids. Pouch 70 has a tongue 82 extending from its front end that incorporates a channel 83 that communicates with inlet port 84. Tongue 82 fits through an aperture in tray 76. The liquid solution is injected into the reservoir pouch through inlet port 84 which is then sealed. A tongue 86 extends from the front end of reservoir pouch 70 and it has a structure similar to that of tongue 82. A channel 88 extends from outlet port 87 to the front end of tongue 86. When reservoir pouch 70 is inserted into chamber A, tongue 86 is inserted downwardly through aperture 76 so that the front end of channel 88 would be in communication with a collector 74, which in this case is a blotter. A strip of filter material is sealed in-between the reservoir layers, across the length of the reservoir and into the outlet tongue. The filter material removes large debris which might clog the outlet channel and aides in the complete emptying of the reservoir.

Self-powered electrochemical micropump 80 is positioned inside collar 71 with its bottom end contacting the top surface of reservoir pouch 70 immediately above aperture 89. Aperture 89 is formed in a transparent film 85, that allows viewing of the reservoir, whose edges are sealed to the top surface of reservoir pouch 70 thereby forming a compartment between them. The annular flange 91 on the base of self-powered electrochemical micropump 80 is sealed around aperture 89.

A tab 90 is pulled to remove the insulator that interrupts the electric current of the micropump 80, thereby starting its operation. Also attached to pull tab 90 is a ripcord wire 92 whose distal end is connected to outlet port 87 of the reservoir pouch 70. When ripcord wire 92 is pulled, the outlet port 87 is opened to allow liquid to travel through channel 88 in tongue 86 allowing it to travel to blotter 74. Gas produced by micropump 80 enters into the transparent compartment, and dispenses fluid from the reservoir pump onto blotter 74. The liquid solution spreads over the high surface area of the blotter and the volatile compounds evaporate through the breathable film bottom wall 78. In this way the elution rate is controlled by flow rate and not diffusion.

What is claimed is:

1. A system for achieving a controlled low emission rate of small volumes of liquid solutions comprising:
   a sealed liquid solution reservoir having an outlet port; said liquid solution reservoir having a small volume capacity in the range of 1–100 Ml;
   a self-powered fluid delivery micropump having means for pumping a liquid solution out of said outlet port of said liquid solution reservoir;
   a collector for receiving a liquid solution from said sealed liquid solution reservoir and for emitting the liquid solution from said collector; said collector having means for producing an emanation rate from said collector that exceeds the fluid delivery rate from said fluid delivery micropump to said collector thus achieving a zero-order emission without accumulation of said liquid solution on said collector and resulting in an emission rate that is constant in time;
   means for opening said outlet port of said sealed liquid reservoir;
   means for transmitting said liquid solution from said outlet port of said liquid solution reservoir to said collector; and
   means to initiate operation of said micropump.

2. A system as recited in claim 1 wherein said self-powered fluid delivery micropump is an electrochemical pump.

3. A system as recited in claim 1 wherein said self-powered fluid delivery micropump is a gas pump.

4. A system as recited in claim 1 wherein said self-powered fluid delivery micropump is an electromechanical pump.

5. A system as recited in claim 1 wherein said self-powered fluid delivery micropump is a mechanical pump.

6. A system as recited in claim 1 wherein said self-powered fluid delivery micropump is a fluid transfer device capable of delivering 1 to 1000 microliters/hour of liquid solution.

7. A system as recited in claim 1 further comprising a liquid solution in said reservoir and said liquid solution only contains chemical agents.

8. A system as recited in claim 1 further comprising a liquid solution in said reservoir and said liquid solution contains chemical agents with solvent, diluent and additives.

9. A system as recited in claim further comprising means for changing the emanation rates from said collector by changing the composition of said liquid solution.

10. A system as recited in claim 1 wherein said means for transmitting a liquid solution from said outlet port of said liquid solution reservoir to said collector is a channel having a front end adjacent said outlet port and a distal end adjacent said collector.

11. A system as recited in claim 1 wherein said means for producing an emanation rate from said collector that exceeds the fluid delivery rate from said fluid delivery micropump to said collector comprising said collector having properties that provide adequate wicking capability to disperse said liquid solution substantially instantaneously without accumulation on said collector.

12. A system as recited in claim 1 wherein all of said system is located in a single container.

13. A system as recited in claim 12 wherein said means for transmitting a liquid solution from said outlet port of said liquid solution reservoir to said collector is a length of tubing having a proximate end and a distal end.

14. A system for achieving a controlled low emission rate of small volumes of liquid solutions comprising:
   a sealed liquid solution reservoir having an outlet port; said liquid solution reservoir having a small volume capacity in the range of 1–100 mL;
   a self-powered fluid delivery micropump having means for pumping a liquid solution out of said outlet port of said liquid solution reservoir;
   a collector for receiving a liquid solution from said sealed liquid solution reservoir and for emitting the liquid solution from said collector;
   means for opening said outlet port of said sealed liquid reservoir;
   means for transmitting said liquid solution from said outlet port of said liquid solution reservoir to said collector in the form of a length of tubing having a proximate end and a distal end;
   means to initiate operation of said micropump; and
   said system is located in a single container; wherein said container has a pair of spaced compartments A and B; said micropump and said sealed liquid solution reservoir being positioned in said compartment A and said collector being positioned in said compartment B; said distal end of said tubing extending into said compartment B.

15. A system as recited in claim 14 wherein said micropump and said sealed liquid solution reservoir are contained in a single assembly.

16. A system as recited in claim 14 wherein said collector is an absorbent pad.

17. A system as recited in claim 16 wherein said absorbent pad has a low emission rate in the range of 0.1–2000 mg/day.

18. A system for achieving a controlled low emission rate of small volumes of liquid solutions comprising:
- a sealed liquid solution reservoir having an outlet port; said liquid solution reservoir having a small volume capacity in the range of 1–100 Ml;
- a self-powered fluid delivery micropump having means for pumping a liquid solution out of said outlet port of said liquid solution reservoir;
- a collector for receiving a liquid solution from said sealed liquid solution reservoir and for emitting the liquid solution from said collector;
- means for opening said outlet port of said sealed liquid reservoir;
- means for transmitting said liquid solution from said outlet port of said liquid solution reservoir to said collector; and means to initiate operation of said micropump;
- said system is located in a single container; and
- means for attaching said container to a support structure.

19. A system for achieving a controlled low emission rate of small volumes of liquid solutions comprising:
- a sealed liquid solution reservoir having an outlet port; said liquid solution reservoir having a small volume capacity in the range of 1–100 mL;
- a self-powered fluid delivery micropump having means for pumping a liquid solution out of said outlet port of said liquid solution reservoir;
- a collector for receiving a liquid solution from said sealed liquid solution reservoir and for emitting the liquid solution from said collector;
- means for opening said outlet port of said sealed liquid reservoir;
- means for transmitting said liquid solution from said outlet port of said liquid solution reservoir to said collector in the form of a channel having a front end adjacent said outlet port and a distal end adjacent said collector;
- means to initiate operation of said micropump; and
- said system is located in a single container; said container has a clam shell tray having a top panel having a rear end, a bottom panel having a rear end and hinge means connecting said respective rear ends together.

20. A system as recited in claim 19 wherein said top panel and/or said bottom panel have a surface having a chamber A formed therein and said bottom panel has a bottom surface having a chamber B formed therein; said sealed liquid solution reservoir being positioned in said chamber A and said collector being positioned in said chamber B.

21. A system as recited in claim 20 wherein said top panel has an upstarting collar having an aperture in its bottom end that communicates with chamber A; said self-powered fluid delivery micropump being located in said aperture.

22. A system as recited in claim 20 wherein said collector is an absorbant pad.

23. A method for achieving a controlled low emission rate for small volumes of chemical agents and liquids such as fragrances, insect formulations, sanitizers, disinfectants, repellents, aromatherapeutic formulations, and any other such liquid requiring delivery in a controlled manner comprising:
- (A) preparing a liquid solution containing one or more chemical agents;
- (B) introducing said liquid solution into a sealed reservoir having an outlet port;
- (C) opening said outlet port;
- (D) initiating the operation of a fluid delivery micropump to pump said liquid solution out of said sealed reservoir onto a collector; and
- (E) emanating said chemical agents from said collector into a surrounding environment at an emanation rate that exceeds the fluid delivery rate from said fluid delivery pump to said collector thus achieving a zero-order emission without accumulation of said liquid solution on said collector and resulting in an emission rate that is constant in time.

24. A method as recited in claim 23 wherein step (B) comprises:
- (a) said sealed reservoir has a small volume capacity of liquid solution in range of 1–100 mL.

25. A method as recited in claim 24 wherein step (D) comprises:
- (a) said micropump is capable of delivering 1–1000 microliters/hour of liquid solution.

26. A method as recited in claim 25 wherein step (E) comprises:
- (a) said collector is capable of low emission rates in the range of 0.1 to 2000 mg/day.

27. A method as recited in claim 26 wherein said collector is an absorbant pad.

28. A method as recited in claim 26 wherein said micropump and said sealed reservoir are a single assembly.

29. A method as recited in claim 26 wherein said micropump, said sealed reservoir, and said collector are located in a single container.

30. A method as recited in claim 26 wherein said liquid solution has multiple chemical agents and they have different mission rates.

* * * * *